US006570954B2

(12) United States Patent
Rasche et al.

(10) Patent No.: US 6,570,954 B2
(45) Date of Patent: May 27, 2003

(54) X-RAY DEVICE FOR TOMOSYNTHESIS

(75) Inventors: Volker Rasche, Hamburg (DE); Erhard Paul Artur Klotz, Neumuenster (DE); Reiner Koppe, Uetersen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/050,252

(22) Filed: Jan. 16, 2002

(65) Prior Publication Data
US 2002/0181649 A1 Dec. 5, 2002

(30) Foreign Application Priority Data
Jan. 19, 2001 (DE) ........................................ 101 02 324

(51) Int. Cl.[7] ................................................ H05G 1/60
(52) U.S. Cl. .............................. 378/21; 378/22; 378/23; 378/25; 378/26
(58) Field of Search .............................. 378/21, 22, 23, 378/25, 26, 57, 58

(56) References Cited

U.S. PATENT DOCUMENTS

| | | | | |
|---|---|---|---|---|
| 5,583,904 A | * | 12/1996 | Adams | 378/22 |
| 6,028,910 A | * | 2/2000 | Kirchner et al. | 378/22 |
| 6,067,341 A | * | 5/2000 | Horiuchi | 378/8 |
| 6,091,797 A | * | 7/2000 | Xie et al. | 378/62 |
| 6,173,033 B1 | * | 1/2001 | Klingenbeck-Regn et al. | 378/20 |
| 6,196,715 B1 | * | 3/2001 | Nambu et al. | 378/197 |
| 6,198,790 B1 | * | 3/2001 | Pflaum | 378/9 |
| 6,249,568 B1 | * | 6/2001 | Rizo et al. | 378/98.12 |
| 6,292,534 B1 | * | 9/2001 | Linders et al. | 378/98.2 |
| 6,324,249 B1 | * | 11/2001 | Fazzio | 378/22 |
| 6,341,156 B1 | * | 1/2002 | Baetz et al. | 378/98.8 |

FOREIGN PATENT DOCUMENTS

DE 19756697 7/1999 .......... G01N/23/06

* cited by examiner

Primary Examiner—Drew A. Dunn
Assistant Examiner—Allen C. Ho
(74) Attorney, Agent, or Firm—John Vodopia

(57) ABSTRACT

An X-ray device for the formation of slice images of an object to be examined including an X-ray source, an X-ray detector, a transport device for moving the object during the acquisition of a series of X-ray projection images of the object in a movement plane situated parallel to the imaging plane, and a control device for controlling the acquisition of the X-ray projection images and the transport device. Slice images of the object are formed from the X-ray projection images by a tomosynthesis method. In order to enable the formation of slice images of large objects to be examined, or of large parts thereof, within a period of time which is as short as possible, the X-ray source and the X-ray detector are stationary during the acquisition of the X-ray projection images and the control device is configured such that the speed of motion of the object and the moments of acquisition of the X-ray projection images are such that all points to be examined in an examination zone of the object are imaged in at least 10, but preferably in at least 50 different X-ray projection images.

20 Claims, 2 Drawing Sheets

X-RAY DEVICE FOR TOMOSYNTHESIS

FIELD OF THE INVENTION

The invention relates to an X-ray device for the formation of slice images of an object to be examined which includes an X-ray source, an X-ray detector, a transport device for moving the object to be examined during the acquisition of a series of X-ray projection images of the object to be examined in a movement plane situated parallel to the imaging plane, and a control device for controlling the acquisition of the X-ray projection images and the transport device. Slice images of the object to be examined are formed from the X-ray projection images by a tomosynthesis method.

The invention also relates to a corresponding method for forming slice images of an object to be examined.

BACKGROUND OF THE INVENTION

The formation of slice images by tomosynthesis is known in the art. The X-ray source and the X-ray detector are moved in opposite directions in parallel planes for the acquisition of X-ray projection images of an object to be examined that is arranged between the planes. This movement is performed such that a projection line between the X-ray source and the X-ray detector, that is, the connecting line between a focal point of the X-ray source and the center of the X-ray detector, extends through the same point of the object to be examined for each X-ray projection image. Different slice images can then be formed by simple addition of the image values that are associated with a voxel of a slice to be imaged of the object to be examined in different X-ray projection images. The object to be examined itself is not moved during the acquisition of the X-ray projection images.

German Patent Publication No. DE 197 56 697 A1 describes a device for X-ray tomosynthesis of parcels. A parcel is moved linearly through an X-ray system by means of a transport device. The X-ray system includes at least three X-ray scanning units whose fan beams are configured such that the parcel is simultaneously irradiated at different angles.

According to the known method, in all cases only the examination of a very limited part of the object to be examined is possible. For the examination and the formation of slice images of large objects, the method must be carried out several times in different regions of the object to be examined, after which the separately formed slice images can be combined, if desired. However, it is desirable to enable the inspection of large areas of the object to be examined merely by way of a single execution of the method and to form slice images of a large area within the shortest possible period of time, for example, the formation of whole body slice images of a patient or slice images of large pieces of luggage in the case of a luggage inspection application.

OBJECTS AND SUMMARY OF THE INVENTION

Therefore, it is an object of the invention to provide an improved X-ray device and a method in which slice images of large examination zones can be formed within a short period of time.

This object is achieved in a device and method in accordance with the invention by arranging the X-ray source and the X-ray detector to be static, i.e., stationary, during the acquisition of the X-ray projection images and configuring the control device such that the speed of the motion of the object to be examined and the instants or moments of acquisition of the X-ray projection images are selected such that all points to be imaged in an examination zone of the object to be examined are imaged in at least 10, but preferably in at least 50, different X-ray projection images.

The invention is based on the recognition of the fact that it is advantageous to move the object to be examined, that is, the patient or the piece of luggage to be inspected, instead of the X-ray source and the X-ray detector during the acquisition of the X-ray projection images. The moments of acquisition of the X-ray projection images and the speed of movement of the object to be examined are then optimized for the relevant tomosynthesis method, preferably being of the digital type in the present case, such that each point of the examination zone to be imaged in the object to be examined appears in at least a minimum number of X-ray projection images, this minimum number amounting to at least 10, but preferably to at least 50 or even from 100 to 200, so as to achieve an adequate image quality. This number, however, is dependent to a high degree on the type, on the condition and on the size of the object to be examined. This makes it possible to form slice images of large objects after a single execution of the method in accordance with the invention, for example, whole body slice images of a patient as they are necessary for trauma scanning. Moreover, the X-ray device and the method in accordance with the invention can be used for the testing of materials and for the inspection of luggage; integration in an existing processing chain is then also possible.

In order to optimize the tomosynthesis angle, that is, the angle of aperture of the X-ray beam that emanates from the X-ray source so as to traverse the object to be examined and be incident on the X-ray detector, the distance between the X-ray source and the X-ray detector can be varied in one embodiment in accordance with the invention. It is also possible to adapt the position of the X-ray source in a direction that is perpendicular to the detector plane, corresponding to the imaging plane, while the X-ray detector is arranged so as to be stationary. Consequently, the tomosynthesis angle can be optimized such that the image quality is optimized. The larger the tomosynthesis angle, the better the image quality will be. The position of the X-ray source, however, preferably is not changed during the acquisition of the X-ray projection images.

In a further preferred embodiment of the invention, at least two series of X-ray projection images are acquired while the X-ray source occupies a different position each time. Preferably, the X-ray source is then asymmetrically arranged relative to the detector, that is, for example, such that it faces the left edge zone of the detector during the acquisition of the first series and the right edge zone of the detector during the acquisition of the second series. This embodiment enables a further optimization of the tomosynthesis angle and hence the image quality.

The tomosynthesis angle can be optimized even further by means of at least one further X-ray detector that is included in a further embodiment of the invention and is arranged adjacent the first X-ray detector.

Preferably, in accordance with the invention, the transport device is moved at an irregular speed and in different, changing directions for the acquisition of the X-ray projection images. It has been found that the formation of artefacts in the slice images can be reduced or even avoided when the object to be examined is not rectilinearly and continuously moved at the same speed through the X-ray beam during the acquisition of the X-ray projection images, but is moved in a kind of "chaotic" way while the speed and the direction of movement change continuously. It may even be advantageous to move the transport device manually and completely irregularly, because the fewest imaging defects and artefacts then occur.

Further advantageous embodiments are disclosed below. It is to be noted that the method for the formation of slice images in accordance with the invention may be elaborated in an identical or similar way as the X-ray device described above and may be realized in versions as described above for the X-ray device in accordance with the invention and as disclosed below.

BRIEF DESCRIPTION OF THE DRAWINGS

The invention will be described in detail hereinafter with reference to the drawings wherein.

DETAILED DESCRIPTION OF THE INVENTION

Figure 1:
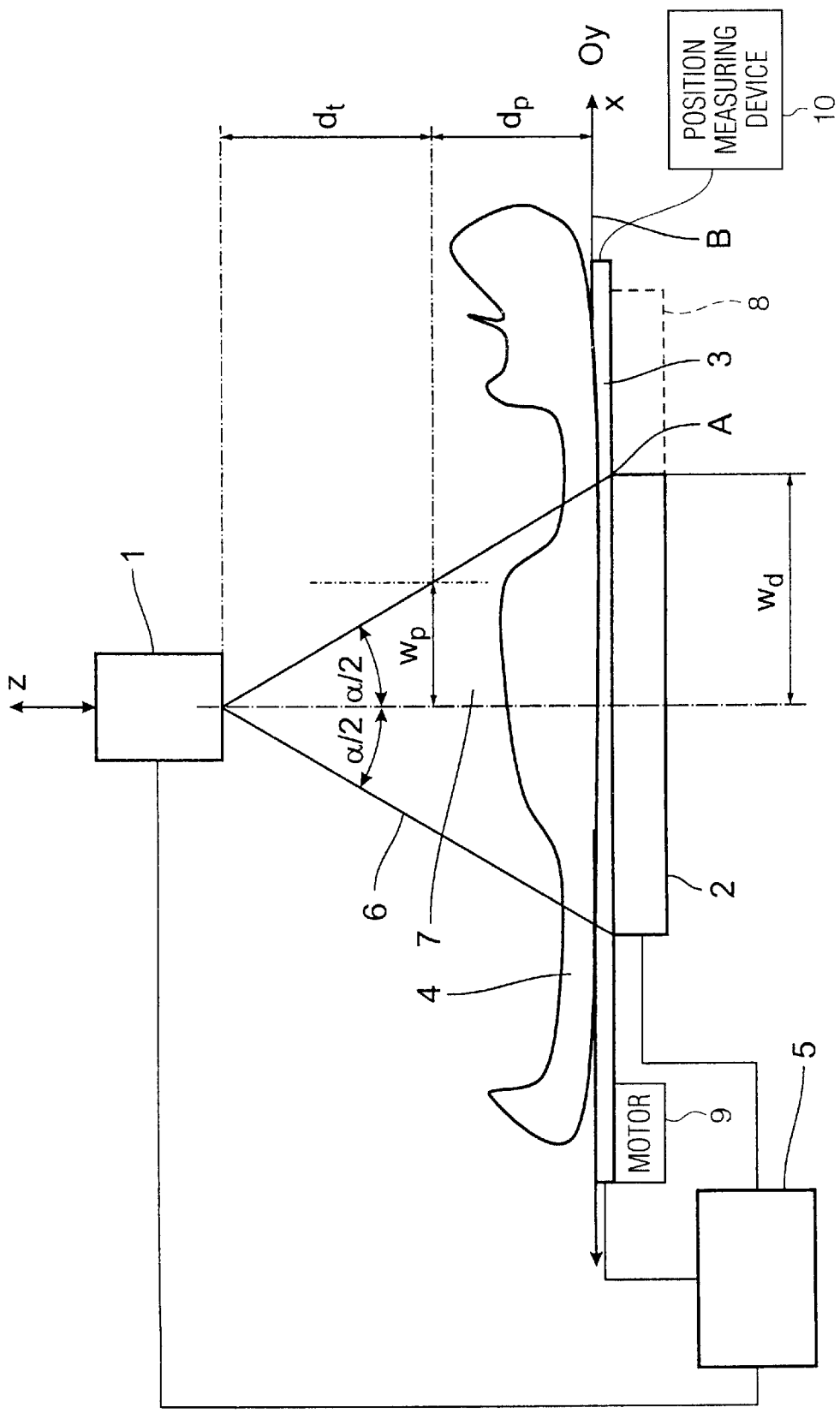
FIG. 1 is a diagrammatic representation of an X-ray device in accordance with the invention.

The X-ray device that is shown in FIG. 1 is provided with an X-ray source 1 and a preferably flat, two-dimensional X-ray detector 2 (which may also be an image intensifier) between which a patient 4 is arranged on a transport device 3, i.e., a patient table in the present case. The transport device 3 with the patient 4 is moved in the plane of motion B, that is, in the x direction and/or the y direction for the acquisition of X-ray projection images, so that a conical X-ray beam 6 generated by the X-ray source successively traverses different regions of the patient 4, these regions then being imaged in the imaging plane A on the X-ray detector 2. The motion of the patient 4 is then controlled, like the X-ray source 1 and the X-ray detector 2, by a control device 5. The X-ray source 1 and the X-ray detector 2 are arranged so as to be statical, i.e., stationary, for the acquisition of the X-ray projection images. However, the position of the X-ray source 1 can be varied in the z direction in order to optimize the tomosynthesis angle $\alpha$.

The image quality of the slice images formed by means of tomosynthesis is then dependent essentially on the tomosynthesis angle ax and on the number n of X-ray projection images that are formed during the data acquisition for a point to be imaged in the examination zone. The tomosynthesis angle a results from the width $w=2w_d$ of the detector 2 and the distance $d=d_t+d_p$ between the X-ray detector 2 and the X-ray source 1 as:

$$\alpha = 2\tan^{-1}(w_d/d).$$

The number n of projection images results from the time $t_b$ during which the point to be imaged is situated within the X-ray beam 6 and from the image rate $f_r$ of the detector as:

$$n = f_r t_b.$$

The time $t_b$ results from the speed $v_t$ of the transport device 3 and from the position z of the point along the connecting axis 7 between the X-ray source 1 and the X-ray detector 2 as:

$$t_b = (zw)/(dv_t).$$

The maximum speed $v_t^{max}$ is dependent on the imaging rate $f_r$ and on the necessary number n of X-ray projection images and amounts to:

$$v_t^{max} = (zwf_r)/(dn).$$

This will be explained in detail hereinafter on the basis of an example. It is assumed that the maximum height $d_p$ of the patient 4 is $d_p=50$ cm and that z is defined as $z=d-d_p$. The imaging rate $f_r$ of the X-ray detector 2 is assumed to be $f_r=25$ images per second, and the dimensions of the X-ray detector 2 are assumed to be 30 cm×40 cm. In order to achieve an adequate imaging quality, each point of the patient 4 should be imaged at least n=100 times when the above values are assumed. The following Table contains the maximum speeds that can be used for the moving of the patient 4 and the resultant tomosynthesis angles for an X-ray detector 2 of the type described herein.

| d[mm] | $W_p$[mm] | $\alpha$[DEG] | $v_t$[mm/s] |
|---|---|---|---|
| 1200 | 233 | 19 | 58 |
| 1000 | 200 | 23 | 50 |
| 800 | 150 | 28 | 37.5 |
| 600 | 67 | 37 | 17 |

Figure 2A:
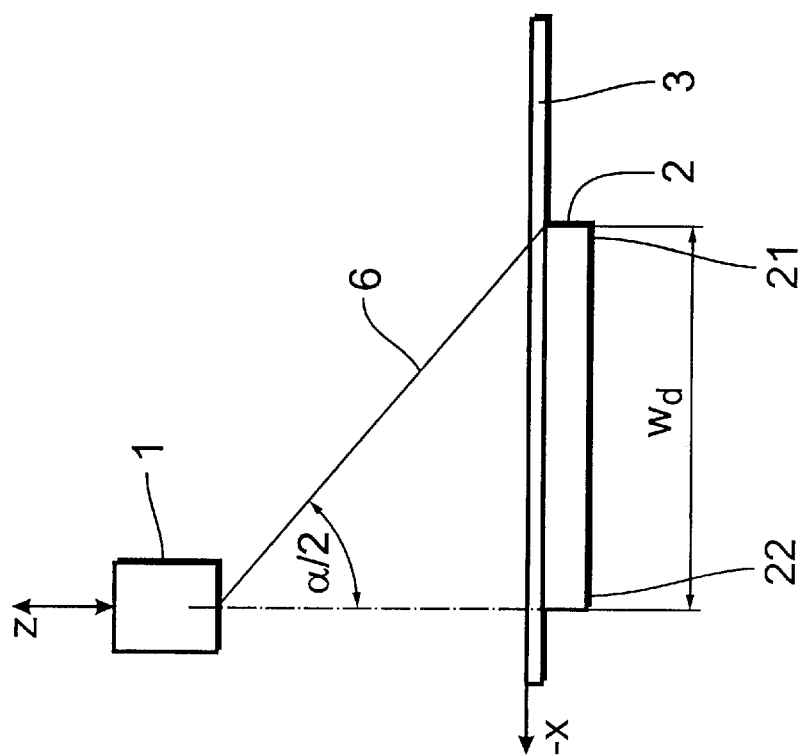
FIGS. 2a and 2b show a further embodiment of an X-ray device in accordance with the invention.
Figure 2B:
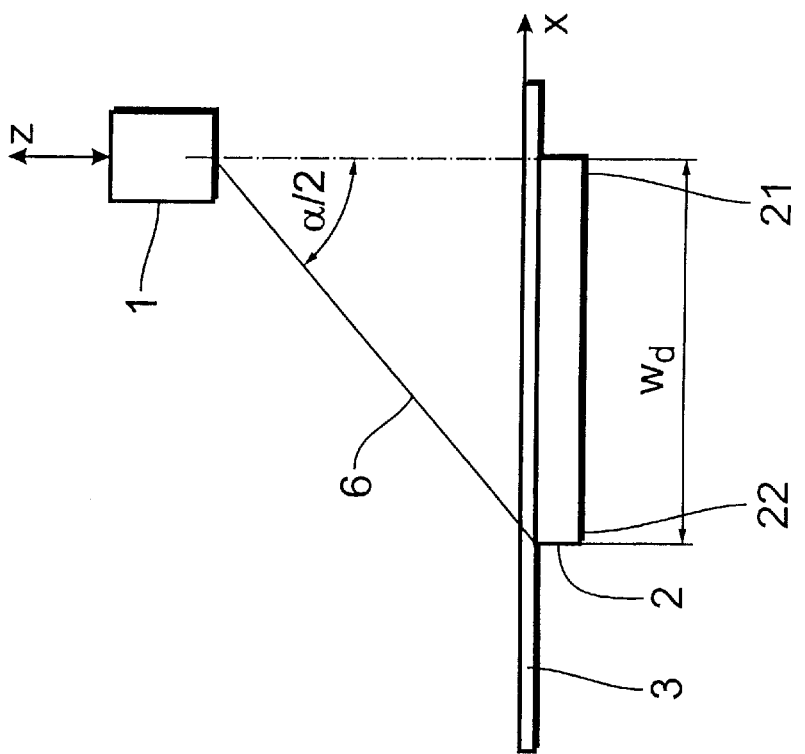

Because the tomosynthesis angle that can be reached is not always large enough to form high-quality tomograms or slice images, further modifications can be carried out on the described construction. For example, as shown in FIGS. 2a and 2b, an asymmetrical arrangement of the X-ray source 1 and the X-ray detector 2 can be used. In order to acquire a first series of X-ray projection images, the X-ray source 1 is arranged to face the right-hand edge zone 21 of the detector 2 (as shown in FIG. 2a), whereas for the acquisition of a second series of X-ray projection images the X-ray source 1 is arranged to face the left-hand edge zone 22 of the detector 2. The direction of movement of the transport device 3 is then inverted during the second step. The tomosynthesis angle a can be doubled when use is made of such an arrangement. It is also possible in principle to acquire more than two series of X-ray projection images in order to increase the tomosynthesis angle even further.

Instead of using a single detector, one or more additional detectors 8 may be employed so as to increase the detector area (as shown in FIG. 1). This may be done for the configuration that is shown in FIG. 1 as well as for that shown in FIGS. 2a and 2b. In the latter case, maximum tomosynthesis angles of between 90° (for $d_t=100$ mm) and 62° (for $d_t=500$ mm) are obtained for a configuration that consists of two detectors while tomosynthesis angles of from 107° (for $d_t=100$ mm) to 78° ($d_t=500$ mm) are obtained for a configuration that consists of four detectors.

In order to avoid the formation of artefacts, instead of using motor control for the movement of the patient during the acquisition of the projection images (via motor 9), it is also possible to move the patient table with the patient manually and completely irregularly, that is in random directions of movement. Nevertheless, all points of the patient to be imaged should then be traversed an adequate number of times by the X-ray beam 6.

Preferably, there are also provided means 10 for measuring the instantaneous position of the transport device for the patient. Such means 10 are preferably provided in the transport device 3 itself, for example, in the form of potentiometers whose measured value is proportional to the instantaneous position of the transfer device 3. Such position measurement is used for the control of the movement of the object 4 to be examined and for the control of the moments of acquisition of the X-ray projection images.

The invention can be used not only for medical purposes but is also suitable for the testing of materials or for the inspection of luggage; for example, it can be integrated in the manufacturing process for a conveyor belt or a transport system.

What is claimed is:

1. An X-ray device for the formation of slice images of an object to be examined, comprising:
   an X-ray source,
   a first X-ray detector,
   a transport device for moving the object during the acquisition of at least first and second series of X-ray projection images of the object in a movement plane parallel to an imaging plane, and
   a control device for controlling the acquisition of the X-ray projection images and the transport device, slice images of the object being formed from the X-ray projection images by a tomosynthesis method,
   the X-ray source and the first X-ray detector being stationary during the acquisition of the X-ray projection images,
   the control device being configured such that the speed of motion of the object and the moments of acquisition of the X-ray projection images are selected such that all points to be imaged in an examination zone of the object are imaged in at least 10 different X-ray projection images,
   the X-ray source being arranged in different positions for the acquisition of the first and second series of X-ray projection images such that an asymmetrical arrangement of the X-ray source and the X-ray detector is formed for the acquisition of the first and second series of X-ray projection images.

2. An X-ray device as claimed in claim 1, wherein the speed of movement of the object and the moments of acquisition of the X-ray projection images are adjusted such that all points to be imaged in an examination zone of the object are imaged in from 100 to 200 different X-ray projection images.

3. An X-ray device as claimed in claim 1, wherein the distance between the X-ray source and the first X-ray detector is variable.

4. An X-ray device as claimed in claim 1, wherein the X-ray source is arranged to face a first edge zone of the X-ray detector for the acquisition of the first series of X-ray projection images and to face a second edge zone of the X-ray detector for the acquisition of the-second series of X-ray projection images, the first edge zone being situated on an opposite side of the X-ray detector from the second edge zone.

5. An X-ray device as claimed in claim 1, further comprising at least one additional X-ray detector arranged adjacent the first X-ray detector for the acquisition of X-ray projection images.

6. An X-ray device as claimed in claim 1, wherein the transport device is manually movable and the X-ray device further comprises means for measuring the position of the transport device.

7. An X-ray device as claimed in claim 1, wherein the transport device ismmovable at a variable speed and in different, changing directions during the acquisition of the X-ray projection images.

8. An X-ray device as claimed in claim 1, wherein the speed of movement of the object and the moments of acquisition of the X-ray projection images are adjusted such that all points to be imaged in an examination zone of the object are imaged in at least 50 different X-ray projection images.

9. An X-ray device as claimed in claim 1, wherein the transport device is movable by means of a motor and the X-ray device further comprises means for measuring the position of the transport device.

10. An X-ray device as claimed in claim 1, wherein the transport device is manually movable during the acquisition of the X-ray projection images.

11. An X-ray device as claimed in claim 1, wherein the transport device is movable in random directions of movement during the acquisition of the X-ray projection images.

12. An X-ray device as claimed in claim 1, wherein an angle of aperture of an X-ray beam from the X-ray source is variable.

13. A method for forming slice images of an object to be examined, comprising:
    placing the object on a transport device,
    arranging an X-ray source in a first position relative to an X-ray detector and acquiring a first series of X-ray projection images of the object by moving the transport device in a controlled manner between the X-ray source and the X-ray detector and in a movement plane parallel to an imaging plane between the X-ray source and the X-ray detector while operating the X-ray source and X-ray detector,
    arranging the X-ray source in a second, different position relative to the X-ray detector and acquiring a second series of X-ray projection images of the object by moving the transport device in a controlled manner between the X-ray source and the X-ray detector,
    selecting the first and second positions of the X-ray source relative to the X-ray detector such that an asymmetrical arrangement of the X-ray source and the X-ray detector is formed for the acquisition of the first and second series of X-ray projection images,
    forming slice images of the object from the X-ray projection images by a tomosynthesis method,
    maintaining the X-ray source and the X-ray detector stationary during the acquisition of the X-ray projection images, and
    selecting the speed of motion of the object and the moments of acquisition of the X-ray projection images such that all points to be imaged in an examination zone of the object are imaged in at least 10 different X-ray projection images.

14. A method as claimed in claim 13, wherein the speed of motion of the object and the moments of acquisition of the X-ray projection images are selected such that all points to be imaged in an examination zone of the object are imaged in at least 50 different X-ray projection images.

15. A method as claimed in claim 13, wherein the transport device is moved in a non-rectilinear and non-continuous manner at a variable speed during the acquisition of at least one of the first and second series of X-ray projection images.

16. A method as claimed in claim 13, wherein the step of selecting the first and second positions of the X-ray source comprises arranging the X-ray source to face a first edge zone of the X-ray detector for the acquisition of the first series of X-ray projection images and to face a second edge zone of the X-ray detector for the acquisition of the second series of X-ray projection images, the first edge zone being situated on an opposite side of the X-ray detector from the second edge zone.

17. A method as claimed in claim 13, wherein the transport device is moved manually during the acquisition of the X-ray projection images.

18. A method as claimed in claim 13, further comprising arranging a plurality of the X-ray detectors adjacent one another opposite the X-ray source.

19. An X-ray device for the formation of slice images of an object to be examined, comprising:
  an X-ray source,
  a first X-ray detector and at least one additional X-ray detector arranged adjacent the first X-ray detector,
  a transport device for moving the object during the acquisition of a series of X-ray projection images of the object in a movement plane parallel to an imaging plane, and
  a control device for controlling the acquisition of the X-ray projection images and the transport device, slice images of the object being formed from the X-ray projection images by a tomosynthesis method,
  the X-ray source and the X-ray detectors being stationary during the acquisition of the X-ray projection images,
  the control device being configured such that the speed of motion of the object and the moments of acquisition of the X-ray projection images are selected such that all points to be imaged in an examination zone of the object are imaged in at least 10 different X-ray projection images.

20. A method for forming slice images of an object to be examined, comprising:
  placing the object on a transport device,
  acquiring a series of X-ray projection images of the object by moving the transport device in a non-rectilinear and non-continuous manner at a variable speed between an X-ray source and an X-ray detector and in a movement plane parallel to an imaging plane between the X-ray source and the X-ray detector while operating the X-ray source and X-ray detector,
  forming slice images of the object from the X-ray projection images by a tomosynthesis method,
  maintaining the X-ray source and the X-ray detector stationary during the acquisition of the X-ray projection images, and
  selecting the speed of motion of the object and the moments of acquisition of the X-ray projection images such that all points to be imaged in an examination zone of the object are imaged in at least 10 different X-ray projection images.

* * * * *